United States Patent [19]

Schmid et al.

[11] Patent Number: 4,552,702
[45] Date of Patent: Nov. 12, 1985

[54] PROCESS FOR THE PREPARATION OF FATTY ACID ALKYL ESTERS HAVING IMPROVED PROCESSING PROPERTIES

[75] Inventors: Karl Schmid, Mettmann; Horst Baumann, Leichlingen, both of Fed. Rep. of Germany

[73] Assignee: Henkel Kommanditgesellschaft auf Aktien, Duesseldorf, Fed. Rep. of Germany

[21] Appl. No.: 397,095

[22] Filed: Jul. 12, 1982

[30] Foreign Application Priority Data

Jul. 20, 1981 [DE] Fed. Rep. of Germany ....... 3128646

[51] Int. Cl.$^4$ ............................. C09F 5/10; C11B 3/00
[52] U.S. Cl. ..................................... 260/428; 260/420; 260/410.9 R
[58] Field of Search ................ 260/428, 420, 410.9 D, 260/410.9 E

[56] References Cited

U.S. PATENT DOCUMENTS

| | | | |
|---|---|---|---|
| 1,981,605 | 11/1934 | Schellmann | 260/420 |
| 3,194,822 | 7/1965 | Neiswender | 260/410.9 E |
| 3,512,994 | 5/1970 | Brown et al. | 260/410.9 E X |
| 3,558,679 | 1/1971 | Queval | 260/410.9 E X |
| 3,758,533 | 9/1973 | Lee | 260/428 |
| 3,857,866 | 12/1974 | Gibble et al. | 260/428 X |
| 3,895,042 | 7/1975 | Taylor | 260/428 X |
| 4,049,686 | 9/1977 | Ringers | 260/428 X |
| 4,327,030 | 4/1982 | McVay et al. | 260/420 X |

FOREIGN PATENT DOCUMENTS 1131835 6/1962 Fed. Rep. of Germany .
1214212 4/1966 Fed. Rep. of Germany .

Primary Examiner—Helen M. S. Sneed
Attorney, Agent, or Firm—Ernest G. Szoke; Nelson Littell, Jr.; Henry E. Millson, Jr.

[57] ABSTRACT

Lower alkyl esters of higher fatty acids with improved processing properties, particularly sulfonation, are obtained by subjecting lower alkyl esters of higher fatty acids of plant and/or animal origin, or said fatty acids per se, in the presence of esterification catalysts and/or carboxylic acid anhydrides, to a brief temperature treatment above 150° C., and separating simultaneously and/or subsequently, preferably by distillation, the purified lower alkyl esters of higher fatty acids or the purified higher fatty acids from the treated material and the purified higher fatty acids are then esterified with lower alkanols.

19 Claims, No Drawings

PROCESS FOR THE PREPARATION OF FATTY ACID ALKYL ESTERS HAVING IMPROVED PROCESSING PROPERTIES

BACKGROUND OF THE INVENTION

This invention relates to a process for the preparation of lower alkyl esters of higher fatty acids having improved properties for processing into surface-active α-sulfo-fatty acid esters.

The preparation of surface-active α-sulfo-fatty acid esters from fats and oils especially of natural origin, has been known for years. For example, U.S. Pat. No. 2,195,187 describes α-sulfo-fatty acids and their esters as surface-active compounds or surfactants. They are obtained by the sulfonation of lower alkyl esters of saturated higher fatty acids with sulfur trioxide. The lower alkyl esters of higher fatty acids are obtained by reesterification of hydrogenated fats or oils with monovalent, lower alkanols, especially methanol, or by the cleavage of glycerides and subsequent esterification of the fatty acids.

Henkel KGaA has been concerned intensively with this class of surface-active α-sulfonated fatty acids and respective fatty acid esters as well as their salts. The German Published Application DE-AS No. 12 46 718, for example, describes a process for the preparation of this class of compounds. Fatty acids and fatty acid esters that have 6 to 28 carbon atoms in the fatty acid radical, have no other groups that can be sulfonated or sulfated beside the carbon atom in α-position, and have an iodine number of less than 5, are sulfonated with a mixture of sulfur trioxide and inert gas, and the reaction product is neutralized. A parallel procedure working with the same substances is described in DE-AS No. 12 48 645.

One of the main problems of the area involved here is the color instability of the lower alkyl esters of higher fatty acids in the sulfonation step. The crude products obtained are dark colored, brown-black and must be processed into light-colored products for use in washing and cleaning agent compositions. While the color of the crude sulfonation products does depend to some degree on the working conditions, the technical utilization of these, of themselves interesting possible starting materials, still is hampered by the following principle: The higher the yield of the reaction in the sulfonation step (the degree of sulfonation), the darker the color of the reaction product and the greater the problems to obtain light-colored end products.

The significance of the constitution of the fatty acids or the fatty acid mixtures to be sulfonated is considered as certain knowledge by the experts in the field. Especially the stipulation is made that the fatty acids to be sulfonated in the α-position shall not have any double bonds, or as few as possible, nor any other types of reactive groups, especially hydroxyl groups. With the selection of suitable fats or oils, this problem is limited to the removal of unsaturated bonds in the fatty acid molecule. These sources of interference are eliminated by hydrogenating the starting material as completely as possible before the sulfonation. The literature of the state of the art indicates required iodine numbers of less than 5, preferably less than 2. Much lower iodine numbers, that is, those in the range from 0.1 to 0.3, are used in the practical examples.

The removal of interfering accompanying substances by distillation or other methods from the fatty acids or fatty acid mixtures to be sulfonated is called for to reduce the discoloration problem, for example in DE-AS No. 12 48 645.

However, bleaching of the crude sulfonic acid derivatives always is necessary as final step in the process. The state of the art has evolved particularly two types of procedures for this purpose: Acid bleaching with hydrogen peroxide, as described in German Patent DE-PS No. 11 79 931, or combination bleaching in which the initial hydrogen peroxide bleaching is followed by the neutralization of the sulfonated and partially bleached material, after which a final bleaching step is conducted, again with hydrogen peroxide or, more advantageously, with hypochlorite, as described in DE-AS No. 12 34 709, for example.

The problem of discoloration becomes particularly difficult when the sulfonation is to be increased to yields exceeding 90%, or even to degrees of sulfonation above 95%. The teachings of the DE-OS No. 14 43 995 concern themselves with the problems arising from this. According to information in this published patent specification, sulfur trioxide has a strongly decomposing effect on saturated fatty acid esters free of alcoholic hydroxyl groups, and this results unavoidably in very dark, discolored sulfonation products in the preparation of highly sulfonated products with a degree of sulfonation of at least 90%, preferably 94%, and especially at least 96%.

DE-OS No. 14 43 995 recommends the addition of water to the sulfonation or the sulfonation product in order to keep the discoloration within limits. But this method generates new problems for the practical application in addition to observing certain temperatures. The viscosity of the sulfonated starting product in the strongly acid range is seriously affected by smallest amounts of water. Even the addition of 2% hydrogen peroxide in the form of a 35% solution causes a steep rise in viscosity with sulfonation products having a chain length of $C_{16}/C_{18}$. The danger of clogged lines can happen in the continuous technical-scale process.

According to the available experience, the various difficulties developing in different steps of the entire process force a compromise between the degree of sulfonation and bleaching. The optimal degree of sulfonation obtainable in practice are close to approximately 90%.

It is common knowledge that natural starting materials such as plant and/or animal fats or oils generally are subject to certain variations in quality, due, for example, to the peculiarities of their origin and/or their handling up to the planned further processing. These variations bring with them a certain increase in problems in further processing, in contrast to standardized, purely synthetic starting materials. Consequently, there exists in the respectively more circumscribed field of the lower alkyl esters of higher fatty acids, a need for the standardization of the product quality of different starting materials by a simple refining procedure as well as for improvement of the processing characteristics of the refined materials, which guarantees dependable and improved subsequent processing results and/or products with improved characteristics in the large-scale operation.

OBJECTS OF THE INVENTION

An object of the present invention is the development of a process for the preparation of lower alkyl esters of higher fatty acids with improved processing properties by a simple refining procedure.

Another object of the present invention is the development of a process for the preparation of lower alkyl esters of higher fatty acids with improved processing properties comprising the steps selected from the group consisting of (A) subjecting lower alkyl esters of higher fatty acids of plant and/or animal origin, to a heat treatment above 150° C., in the presence of an effective amount to reduce the hydroxyl number of a material selected from the group consisting of esterification catalysts and carboxylic acid anhydrides, for a time sufficient to effect an improvement in further processing properties, separating purified lower alkyl esters of higher fatty acids from the treated material and recovering said lower alkyl esters of higher fatty acids with improved processing properties, and (B) subjecting free higher fatty acids of plant and/or animal origin to a heat treatment in the presence of an effective amount to reduce the hydroxyl number of a material selected from the group consisting of esterification catalysts and carboxylic acid anhydrides, for a time sufficient to effect an improvement in further processing properties, separating purified higher fatty acids from the treated material, esterifying the purified higher fatty acids with a lower alkanol under esterification conditions, and recovering said lower alkyl esters of higher fatty acids with improved processing properties.

These and other objects of the present invention will become more apparent as the description thereof proceeds.

The invention is based on the objective of the requirement of obtaining a uniform starting material for further processing, particularly by sulfonation, which product has improved processing properties. With it, the described problems of discoloration of alkyl esters of fatty acids or their mixtures during sulfonation are to be reduced, for example. The invention is an attempt to create, in a limited sense, a pretreatment for the alkyl esters of fatty acids to be sulfonated, which makes an effective curtailment of the discoloration in the subsequent sulfonation step possible. On the other hand, the invention is an attempt at the standardization of the fatty acids or alkyl esters of fatty acids from natural sources, by a simple refining procedure, to permit reproducible processing results, for example, during the sulfonation of the alkyl esters of fatty acids. In particular, the invention is also an attempt to adapt starting materials of lower quality to the subsequent purification steps into high-quality materials.

The technical solution of the objects of the invention is based on the discovery that the desired goal is achieved if the alkyl esters of fatty acids are subjected to a thermal pretreatment under specific conditions given below, or if the free fatty acids are subjected to this pretreatment and are subsequently esterified with the corresponding alcohols.

Thus, the subject of the invention is a process for the preparation of lower alkyl esters of higher fatty acids with improved processing properties from higher fatty acids of plant and/or animal origin. The process according to the invention is characterized by the fact (A) that the starting material containing the lower alkyl esters of higher fatty acids is subjected to a relatively brief temperature treatment above 150° C. in the presence of esterification catalysts and/or carboxylic acid anhydrides, and the so-reacted lower alkyl esters of higher fatty acids are separated from the added adjuvants and small amounts of high-boiling substances formed during the treatment, preferably by distillation, or (B) that the starting material containing free higher fatty acids is subjected to a relatively brief temperature treatment in the presence of esterification catalysts and/or carboxylic acid anhydrides, the so-treated higher fatty acids are separated from the added adjuvants and small amounts of high boiling substances formed during the treatment, preferably by distillation, and the purified free higher fatty acids are esterified by lower alkanols in a conventional manner.

More particularly, the present invention relates to a process for the preparation of lower alkyl esters of higher fatty acids with improved processing properties comprising the steps selected from the group consisting of (A) subjecting lower alkyl esters of higher fatty acids of plant and/or animal origin, to a heat treatment above 150° C., in the presence of an effective amount to reduce the hydroxyl number of a material selected from the group consisting of esterification catalysts and carboxylic acid anhydrides, for a time sufficient to effect an improvement in further processing properties, separating purified lower alkyl esters of higher fatty acids from the treated material and recovering said lower alkyl esters of higher fatty acids with improved processing properties, and (B) subjecting free higher fatty acids of plant and/or animal origin to a heat treatment above 150° C. in the presence of an effective amount to reduce the hydroxyl number of a material selected from the group consisting of esterification catalysts and carboxylic acid anhydrides, for a time sufficient to effect an improvement in further processing properties, separating purified higher fatty acids from the treated material, esterifying the purified higher fatty acids with a lower alkanol under esterification conditions, and recovering said lower alkyl esters of higher fatty acids with improved processing properties.

This temperature pretreatment is performed preferably in the range up to approximately 280° C. and especially in the temperature range from about 200° to 250° C. Temperatures in the range from 200° to about 230° C. can be especially advantageous. The treatment conditions and especially the treatment temperature and the time the starting material to be purified remains at this temperature under the process conditions are mutually adjusted, preferably in the manner to be described in the following.

The duration of the pretreatment according to the invention, that is, the time the alkyl esters of the fatty acid or the free fatty acid starting material remains under the treatment conditions, is generally relatively brief. It may last for up to 15 minutes, for example, but considerably shorter times can be used in preferred practical examples of the invention. If needed, the thermal pretreatment according to the invention can be extended, for example, up to 30 minutes or also to about one hour. However, no significant processing advantages are generally connected with this extension.

In the preferred practical example of the invention, the conditions of the refining step according to the invention, and here especially the treatment temperature and the time the material is treated, are mutually adjusted so that an esterification or reesterification of free hydroxyl groups can take place, preferably without any other substantial alteration in the structure of the alkyl esters of the fatty acid or the free fatty acid. This measure according to the invention becomes comprehensible with the following explanation. The alkyl ester of the fatty acid or the free fatty acid starting material apparently contains interfering components, which are present in varying quantities depending on origin and individual history of the respective alkyl ester of the fatty acid or free fatty acid material. These interfering components obviously are compounds that are hydroxylated on the chain, which may be present only in trace quantities but make themselves known by a disproportionate interference during the subsequent processing, possibly after esterification, of the alkyl esters of the fatty acids. With the temperature pretreatment under the given conditions, the process according to the invention is designed to create the possibility of obtaining a standardized, purified alkyl ester of a fatty acid product that does no longer have the described disadvantages in the subsequent processing phases. The pretreatment according to the invention actually allows the separation of smallest quantities of interfering accompanying substances from the fatty acid esters or free fatty acids that are not hydroxylated on the chain by a simple reaction. The esterification or reesterification of the components containing free hydroxyl groups with the ester or carboxyl groupings of the reaction materials present in an excess and/or the reaction with the added carboxylic acid anhydrides brings about such a shift in the boiling point of these interfering admixtures that the separation of the purified main part of the fatty acid esters or free fatty acid starting materials used from the formed high-boiling substances by distillation becomes possible. Alkyl esters of fatty acids or free fatty acids of natural origin usually are mixtures of varying amounts of saturated and unsaturated compounds, as they were obtained from the respective fats or oils of natural origin. Because of their individual histories of preparation and storing, mixing or blending and additional influences of this type, starting materials with widely varying qualifications must be expected in practice. The conversion of any different starting materials, by one constant method, into a product that can be processed more readily in one of the described following processing phases and/or will lead to improved end products, is possible with the pretreatment according to the invention.

The reactive purification according to the invention can be facilitated by working under reduced pressure. Such a reduction in pressure should accelerate the shift in the equilibrium during the reesterification reaction between hydroxyl groups on the chains and the terminally located ester or carboxyl groupings, with the cleavage and removal of the monofunctional alcohol if the alkyl ester of fatty acid is used. In a preferred practical example, the work proceeds at such a reduced pressure that the distillation of the lower alkyl esters of fatty acids or the free fatty acids freed of interfering components becomes possible either simultaneously with or immediately following, the refining treatment according to the invention. For example, working with pressures in the range from 0.05 to 10 torr, particularly in the range from about 0.1 to 5 torr, can be especially advantageous. The combining of the temperature pretreatment according to the invention for the reactive elimination of the interfering components and the separation by distillation of the purified material into a preferably continuously operating phase of the process is possible in this manner. The reactive conversion of the interfering accompanying components into high-boiling substances is accomplished in surprisingly short time spans that may be in the range of seconds or even fractions of a second. For example, it is possible according to the invention to add esterification catalysts and/or carboxylic acid anhydrides to the starting material to be purified and to distill the mixture, while maintaining the pot temperature of the material to be distilled above 150° C. and preferably within the temperature range particularly suitable according to the invention. Thermal pretreatment and separation of the undesirable parts of the product thus are practically combined into one step of the process. Another especially technically simple modification provides that the esterification catalysts and/or carboxylic acid anhydrides, dissolved, for example, in a high-boiling substance, are charged in the temperature range of the pretreatment according to the invention and under reduced pressure. The starting material to be purified is fed into this reaction zone either proportionately or preferably continuously. Pressure and temperature conditions are mutually adjusted to guarantee the distillation of the major part of the fatty acid ester or free fatty acid material. Despite the very fast vaporization of the starting material fed into the reaction zone, the interfering components are converted by reaction at such a rate that the collected distillate has the desired improved processing properties.

Especially in these latter practical examples of the simultaneous reactive purification and distillation, the work may proceed with holding times at the desired temperature in the range from about 0.1 to 3 minutes, for example, with temperatures preferably in the range from about 200° to 250° C.

Esterification catalysts and/or carboxylic acid anhydrides are used as active additives in the process according to the invention. Any esterification catalysts from the extensive present state of the art may be used for this purpose. However, the work is performed preferably with basic, neutral or at most weakly acid catalysts or catalytic systems. Especially preferred is to conduct the work with catalysts that are soluble in the starting material to be purified and/or in high-boiling substances, which are formed during the process according to the invention and/or are used in the purification according to the invention in the sense described above. The use of liquid, soluble catalysts or catalytic systems can be particularly expedient.

The compilation in *J. Am. Oil Chem. Soc.* 55: 796-805, 1978, especially the compilation from Table I on page 797, is cited simply as an example from the extensive state of the art concerning the esterification catalysts. Listed are metal salts such as acetates, carbonates, chlorides, nitrates and oxides of tin, zinc, iron, cobalt and lead; alkali metal hydroxides such as NaOH, KOH, LiOH; metal soaps such as the stearates of alkali metals, zinc, aluminum and titanium; alkali metals or their alloys; metal alkylates and metal hydrides. Especially suitable are metal soaps of saturated and/or unsaturated monocarboxylic or polycarboxylic acids with the carbon chain lengths $C_2-C_{36}$ of the following metals: K, Na, Li, Al, B, Zn, Sn, Ca, Mg, Ti and V; metallic alcoholates of saturated and unsaturated monohydric or polyhydric linear or branched alcohols with the carbon chain length $C_1-C_{36}$ with the following metals as cation: Li, Na, K, Mg, Ca, B, Al, Zn, Sn and Ti; the metal hydrides, that is, hydrogen compounds of the elements Li, Na, Mg, Ca, B, Al and Sn or their mixtures; and the metal alkyls, that is, carbon compounds of the elements Li, Na, Mg, Ca, B, Al, Sn and Ti, or their mixtures.

An especially suitable class of catalysts or active additives is derived from soluble organic compounds of boric acid. Suitable are especially boric acid esters, for example, boric acid alkyl esters, among which those with relatively higher alcohols ($C_{10}$–$C_{22}$, especially $C_{12}$–$C_{18}$-alkanols) can be particularly preferred. But suitable are especially also esters of boric acid with partial esters of polyhydric alcohols, for example, the respective esters of polyhydric alcohols with mono- or diglycerides. These partial esters of polyhydric alcohols may also be derived from higher fatty alcohols, especially those in the carbon atom range of from 10 to 22. Boric acid esters that are liquid and/or soluble at the process temperature are a preferred catalyst class. Additional examples of suitable boric acid compounds are boric acid anhydride, sodium borate and sodium boronate.

Carboxylic acid anhydrides can be used as active additives in addition to, or instead of, esterification catalysts in the temperature treatment according to the invention. However, the concurrent use of esterification catalysts that facilitate the reaction of the carboxylic acid anhydride with hydroxyl groups is preferred. The carboxylic acid anhydrides can be derived basically from monocarboxylic acids or polycarboxylic acids, especially from dicarboxylic acids in this case. In one practical example of the invention, the use of relatively high-boiling carboxylic acid anhydrides with a boiling point especially higher than that of the fatty acid esters or free fatty acids to be refined, is to be preferred. For example, carboxylic acid anhydrides boiling above 300° C./1 torr can be suitable starting materials for the process of the invention. Such carboxylic acid anhydrides are derived, for example, from $C_8$–$C_{28}$-monocarboxylic acids, especially from monocarboxylic acids with 10 to 22 carbon atoms ($C_{10-22}$-fatty acids). Working with such high-boiling carboxylic acid anhydrides facilitates the process according to the invention inasmuch as possibly present excesses of this active additive can be readily removed from the refined fatty acid ester or free fatty acid by a subsequent distillation.

Also included under the term carboxylic acid anhydrides according to the invention are mixed acid anhydrides of carboxylic acids and inorganic acids, especially mixed acid anhydrides of higher fatty acids and boric acid. As explained, the fluidity of the reaction components used as additives may be desirable for the performance of the process according to the invention in a continuous operation. Distillation residues from the known treatment of fatty acids, for example, those of natural origin, with boric acid compounds that contain a not inconsiderable proportion of fatty acid anhydrides, mixed boric acid/fatty acid anhydrides and/or boric acid, are a suitable additive for the refining process according to the invention. These fluid distillation residues thus can be used in an important, further process step.

The mentioned active additives (esterification catalysts and/or carboxylic acid anhydrides) usually are added only in small quantities to the fatty acid ester or free fatty acid starting material to be purified, although larger amounts are generally not harmful. Suitable are, for example, amounts from 0.01 to 20% by weight, especially amounts in the range from about 0.1 to to 10% by weight, of the active additive or additive mixture, calculated with respect to the fatty acid ester or free fatty acid starting material. Amounts of the active additive not exceeding 5% by weight, preferably not exceeding 3% by weight, will generally be used. The especially preferred range for the amount to be used lies between 0.05 and 1.0% by weight. All of these percentages by weight are based on the fatty acid ester or free fatty acid starting material to be treated. When carboxylic acid anhydrides are used together with esterification catalysts, the catalysts may be used in the usual small amounts, for example, their amount is from 0.001 to 10% by weight, especially from 0.01 to 5% by weight, calculated on the carboxylic acid anhydride. When the above described continuous process is used, in which the starting material to be purified is added to a reaction zone containing the esterification catalysts and/or carboxylic acid anhydrides, and purified fatty acid ester or free fatty acid material is simultaneously removed from this reaction zone by distillation, the only thing to be observed is the use of reesterification catalyst and/or carboxylic acid anhydride in an amount that is adequate to bring about the desired reactive removal of the interfering components within the brief time span available for the reaction.

The purification of the lower alkyl esters of higher fatty acids according to the invention does not necessarily result in an improvement in color nor in a substantial change in the parameters (hydroxyl number, iodine number, saponification number and/or acid number). The effect of the pretreatment according to the invention does not manifest itself in the purified lower alkyl esters of higher fatty acids but only with its continued processing, that is, after the sulfonation of a starting material pretreated by this method. In this case, it is expressed in the better bleaching qualities of the sulfonation product, for example. Bleached products with Klett color numbers of less than 60 can be prepared without any problems.

The pretreatment according to the invention can be carried out with fatty acid ester or free fatty acid fractions hardened by hydrogenation or still unhardened. When unhydrogenated material is treated, the obtained product fraction should be hardened as soon as possible to eliminate undesirable oxidative influences due to ageing via the double bonds in the product.

A conventional separation of interfering components, presumably of the portions formed by oxidative ageing causing the hydroxylated methyl ester of fatty acids where the hydroxyls are located on the chain, from the problem-free parts of the starting material is practically impossible. A distillation does not achieve the objective. The teachings of the invention, that is, subjecting the starting material of any composition together with the active additives to the thermal pretreatment and especially distilling above this material, removes the existing difficulties and yields reliably a starting material suitable for the following sulfonation and bleaching.

The knowledge of the state of the art applies to the subsequent sulfonation and bleaching. Details for the performance of the acid bleaching or multiphase combination bleaching are found, for example, in the German patents DE-PS Nos. 11 79 931 and 12 34 709 and the DE-OS No. 14 43 995. The described sulfonation is usually carried out at temperatures from 70° to 130° C. in a descending film reactor with a mixture of gaseous sulfur trioxide and an inert gas, during a period of 10 to 20 minutes and to give sulfonation degrees exceeding 90% especially exceeding 92% and, as a rule, exceeding 94%. Sulfonation degrees of 95% and higher are especially preferred. Yet, sulfonation products with Klett numbers of 50 or less can be prepared reliably with the use of the purification treatment according to the invention.

Suitable higher fatty acid ester starting materials are especially the respective lower alkyl esters with preferably 1 to 5 carbon atoms in the alkanol radical. Especially important are the methyl esters of higher fatty acids that were obtained from plant and/or animal fats by reesterification or by saponification with subsequent esterification.

EXAMPLES

The following examples explain the pretreatment according to the invention and its results along with comparison experiments that lie outside the scope of the invention. These examples are not to be deemed limitative in any respect.

The purification effect of the process according to the invention is judged by the beachability of the ester sulfonate pastes obtained after sulfonation.

The method of sulfonation and bleaching described below applies to all examples:

Batches of 576 gm of a methyl ester of tallow fatty acids were sulfonated in a standing cylinder heated to 80° C. by blowing in, over a period of 65 minutes, a 5% by volume mixture of $SO_3$ in air, in such a rate that the total amount contained 208 gm(=2.6 mol) of $SO_3$, and a subsequent after-reaction period of 15 minutes. The crude sulfonic acid obtained was neutralized by the simultaneous addition of crude sulfonic acid and sodium hydroxide solution together to give a mixture in the pH range from 6.5 to 8 to form a aqueous paste containing about 25% sulfonation product. This sulfonation product was then bleached at 60° C. with 15.4% by weight, based on the sulfonation product, of a 13% aqueous NaOCl solution. A 5% aqueous solution of the sulfonation product, adjusted to pH 7, had a Klett number as mentioned in the individual examples, when it was measured with the blue filter (420 mm) in a Klett round-glass cell on the Klett-photometer (Model 800-3 by Klett-Summerson). The degree of sulfonation of the pastes obtained was between 95 and 97%.

COMPARISON EXAMPLE A

The starting material was a methyl ester of a hardened (hydrogenated) tallow fatty acid, obtained by splitting of tallow, washing out the glycerol, esterification of the tallow fatty acid with methanol, then hardening (hydrogenation of the existing C-C double bonds) and distillation. This methyl ester of a hardened tallow fatty acid had the following values: iodine number 0.3; hydroxyl number 2.0; acid number 0.6; saponification number 194.4, and was sulfonated as described above, neutralized, and bleached. After a bleaching time of 30 minutes, the Klett number of the ester sulfonate paste was 255.

EXAMPLE 1

The hardened methyl ester of tallow fatty acid used in Comparison Example A was distilled before sulfonation by mixing with 0.5% by weight, based on the methyl ester of the fatty acid, of lithium aluminum hydride, and by heating to a sump temperature of 230° C./0.1 mbar. The distillation residue minus the lithium aluminum hydride was 8.5% by weight. The methyl ester of the hardened tallow fatty acid thus purified had the following values: iodine number 0.; hydroxyl number 0; acid number 0.2; saponification number 194.3; and was sulfonated under the above stated conditions, neutralized and bleached. After a bleaching time of 30 minutes, the Klett number of the ester sulfonate paste was 42.

EXAMPLE 2

The hardened methyl ester of tallow fatty acid used in Comparison Example A was distilled before the sulfonation in the presence of 0.5% by weight, based on the methyl ester of the fatty acid, of aluminum chloride, and by heating to a sump temperature of 230° C./0.1 mbar. The distillation residue minus the aluminum chloride was 2.8% by weight. The purified hardened methyl ester of tallow fatty acid had the following values: iodine number 0.2; hydroxyl number 0; acid number 0.2; saponification number 193.8; and was sulfonated as described above, neutralized, and bleached. After a bleaching time of 30 minutes, the Klett number of the ester sulfonate paste was 50.

EXAMPLE 3

The hardened methyl ester of tallow fatty acid used in Comparison Example A was distilled before the sulfonation with an addition of 0.5% by weight, based on the methyl ester of the fatty acid, of sodium-aluminum hydridotrimethylate $NaAlH(OCH_3)_3$; and by heating to a sump temperature of 230° C./0.1 mbar. The distillation residue minus the catalyst was 2.4% by weight. The purified hardened methyl ester of tallow fatty acid had the following values: iodine number 0.2; hydroxyl number 0; acid number 0.3; saponification number 194.2; and was sulfonated as described above, neutralized, and bleached. After a bleaching time of 30 minutes, the Klett number of the ester sulfonate paste was 45.

COMPARISON EXAMPLE B

The starting material was a methyl ester of a hardened (hydrogenated) tallow fatty acid which had been obtained by splitting of tallow, washing out the glycerol, esterification of the tallow fatty acid with methanol, hydrogenation of the existing C-C double bonds, and distillation. This methyl ester of hardened tallow fatty acid had the following values: iodine number 0.2; hydroxyl number 1.8; acid number 0.2; saponification number 194.4; and was sulfonated as described above, neutralized, and bleached. After a bleaching time of 2 hours, the Klett number was 200.

EXAMPLE 4

The methyl ester of the hardened tallow fatty acid used as starting material in Comparison Example B was distilled before the sulfonation in the presence of 5% by weight, based on the methyl ester of fatty acid, of boric acid by heating to a sump temperature of 230° C./0.1 mbar. The distillation residue minus the boric acid present was 0.8% by weight. This methyl ester of tallow fatty acid was sulfonated in the stated manner, neutralized, and bleached. After a bleaching time of 2 hours, the Klett number was 33.

COMPARISON EXAMPLE C

A methyl ester of a hardened tallow fatty acid, obtained as in Comparison Example A, with the values: iodine number 0.3; hydroxyl number 2.0; acid number 0.6; saponification number 194.4, was sulfonated as described before, neutralized, and bleached. After a bleaching time of 4 hours, the Klett number of the ester sulfonate paste was 200.

EXAMPLE 5

The methyl ester of the hardened tallow fatty acid used in Comparison Example C was distilled before the sulfonation in the presence of 2% by weight, based on the methyl ester of the fatty acid, of aluminum stearate by heating to a sump temperature of 230° C./0.1 mbar. The distillation residue minus the aluminum stearate present was 3.5% by weight. The purified methyl ester of hardened tallow fatty acid having an iodine number 0.3; hydroxyl number 0; acid number 0.8; saponification number 194.1, was sulfonated as stated above, neutralized, and bleached. After a bleaching time of 4 hours, the Klett number of the ester sulfonate paste was 50.

EXAMPLE 6

The hardened methyl ester of tallow fatty acid used in Comparison Example C was distilled before the sulfonation with the addition of 1% by weight, based on the methyl ester of the fatty acid, of iron (III) chloride by heating to a sump temperature of 230° C./0.1 mbar. The distillation residue, minus the iron (III) chloride present, was 4.5% by weight. The thus purified methyl ester of hardened tallow fatty acid with an iodine number 0.6; hydroxyl number <1; acid number 0.2; saponification number 194.0 was sulfonated as described above, neutralized, and bleached. After a bleaching time of 4 hours, the Klett number of the ester sulfonate paste was 80.

COMPARISON EXAMPLE D

The starting material was a methyl ester of a hardened tallow fatty acid, obtained by transesterification of tallow with methanol with subsequent distillation and hardening (hydrogenation of existing C-C double bonds). The ester obtained had the values: iodine number 0.55; hydroxyl number <1; acid number 0.4; saponification number 194.0. This ester was sulfonated, neutralized, and bleached. After a bleaching time of 30 minutes, the Klett number of the ester sulfonate paste obtained was 260.

COMPARISON EXAMPLE E

The methyl ester of tallow fatty acid used in Comparison Example D with the iodine number 0.55 was further hardened to an iodine number of 0.1. This ester was sulfonated as described, neutralized, and bleached. After a bleaching time of 30 minutes, the Klett number of the ester sulfonate paste was 180.

EXAMPLE 7

The rehardened methyl ester of tallow fatty acid used in Comparison Example E was distilled before the sulfonation with addition of 0.5% by weight, based on the methyl ester of the fatty acid, of sodium-boron hydride by heating to a sump temperature of 230° C./0.1 mbar. The distillation residue was 2.8% by weight. The thus purified methyl ester of tallow fatty acid was sulfonated as described above, neutralized, and bleached. After a bleaching time of 30 minutes, the Klett number of the ester sulfonate paste obtained was 40.

EXAMPLE 8

To prepare the catalyst, 379 gm of tallow fatty acid and 7.5 gm of boric acid were stirred for 3 hours at 200° C. Then the mixture obtained was distilled by heating to a sump temperature of 280° C./0.1 mbar. There were obtained 82 gm of a residue having a melting point of about 60° C.

The starting material used in Comparison Example E was distilled before the sulfonation in the presence of 1.5% by weight, based on the methyl ester of tallow fatty acid charged, of the catalyst by heating to a sump temperature of 230° C./0.1 mbar. The distillation residue was 3% by weight. The distilled hardened methyl ester of tallow fatty acid was sulfonated in the manner described, neutralized, and bleached. After a bleaching time of 30 minutes, the Klett number of the ester sulfonate paste obtained was 27.

COMPARISON EXAMPLE F

The starting material was a hardened methyl ester of tallow fatty acid, obtained by transesterification of tallow with methanol with subsequent distillation and hardening. This material was subjected to a second distillation. The obtained hardened methyl ester of tallow fatty acid was free from glycerides and had the following values: iodine number 0.25; hydroxyl number 1.0; acid number 0.2; saponification number 196.4. This ester was sulfonated in the described manner, neutralized, and bleached. After a bleaching time of 2 hours, the Klett number of the ester sulfonate paste obtained was 95.

EXAMPLE 9

For the preparation of the catalyst, 500 gm of tallow fatty acid and 2.5 gm of boric acid were stirred for one hour at 200° C./133 mbar, and the mixture was then distilled by heating to a sump temperature of 280° C./0.1 mbar. The residue was 120 gm.

The starting material used in Comparison Examle F was distilled before the sulfonation with addition of 1.3% by weight, based on the methyl ester of fatty acid, of the previously prepared catalyst, by heating to a sump temperature of 230° C./0.1 mbar. The distillation residue was 1.6% by weight. The purified methyl ester of tallow fatty acid was sulfonated as described above, neutralized, and bleached. After a bleaching time of 2 hours, the Klett number of the ester sulfonate paste obtained was 30.

COMPARISON EXAMPLE G

The starting material was a methyl ester of a tallow fatty acid, obtained by transesterification of tallow with methanol followed by distillation and hardening. The hardened material was subjected to a second distillation. The obtained methyl ester of tallow fatty acid was free from glycerides and had the values: iodine number 0.2; hydroxyl number 0.8; acid number 0.6; saponification number 196.6. This hardened methyl ester of tallow fatty acid was sulfonated as described, neutralized, and bleached. After a bleaching time of 30 minutes, the Klett number of the obtained ester sulfate paste was 135.

EXAMPLE 10

For the preparation of the catalyst, 320 gm of a mixture of 45% by weight of glycerol monostearate, 41% by weight of glycerol distearate, and 14% by weight of glycerol tristearate were stirred together with 62 gm of boric acid for 3 hours at 160° C./66.5 mbar. The boric acid dissolved. The reaction product had a melting point of about 50° C.

The starting material used in Comparison Example G was distilled before the sulfonation in the presence of 0.9% by weight, based on the fatty acid ester charged, of the previously prepared catalyst, by heating to a sump temperature of 230° C./0.1 mbar. The distillation residue was 1.7% by weight. The distilled hardened methyl ester of tallow fatty acid was sulfonated in the manner described, neutralized, and bleached. After a bleaching time of 30 minutes, the Klett number of the ester sulfonate paste obtained was 46.

EXAMPLE 11

The starting material used in Comparison Example F was distilled before the sulfonation in the presence of 1.0% by weight, based on the methyl ester of fatty acid, of zinc stearate, by heating to a sump temperature of 230° C./0.1 mbar. The distillation residue was 2.0% by weight. The distilled hardened methyl ester of tallow fatty acid was sulfonated as described, neutralized, and bleached. After a bleaching time of 2 hours, the Klett number of the ester sulfonate paste obtained was 47.

EXAMPLE 12

The starting material used in Comparison Example G was distilled before the sulfonation with an addition of 0.5% by weight, based on the methyl ester of fatty acid, of sodium methylate, by heating to a sump temperature of 230° C./0.1 mbar. The distillation residue was 6.3% by weight. The purified methyl ester of tallow fatty acid was sulfonated as described, neutralized, and bleached. After a bleaching time of 30 minutes, the Klett number of the ester sulfonate paste was 40.

EXAMPLE 13

For the preparation of the catalyst, 379 gm of hardened tallow fatty acid (iodine number 0.3) and 7.5 gm of boric acid were stirred for 3 hours at 200° C., and the mixture was subsequently distilled by heating to a sump temperature of 280° C./0.1 mbar. There were obtained 82 gm of a residue having a melting point of about 60° C.

In the starting material used in Comparison Example E, 1.5% by weight, based on the methyl ester of fatty acid charged, of the catalyst were dissolved. This mixture was transferred continuously, drop by drop, into a distillation flask heated to 230° C. at 0.1 mbar, the inflow having been regulated so that it matched the quantity distilling. The distillation residue was 2% by weight. The methyl ester of tallow fatty acid thus distilled was sulfonated as described before, neutralized, and bleached. After a bleaching time of 30 minutes, the Klett number of the ester sulfonate paste obtained was 50.

EXAMPLE 14

The starting material was an unhardened tallow fatty acid, obtained by splitting of tallow and washing out the glycerol. This tallow fatty acid was distilled in the presence of 1% by weight, based on the fatty acid charged, of sodium boron hydride, by heating to a sump temperature of 230° C./0,1 mbar. The distilled tallow fatty acid was heated with methanol in the weight ratio 1:1.1 in an autoclave for 2 hours at 200° C. Then unreacted methanol was removed by distillation. The residue was again admixed with 1.1 parts by weight of methanol to 1 part tallow fatty acid charged and again heated in the autoclave for 2 hours at 200° C. This operation was repeated once more after the distillation of the unreacted methanol from the reaction mixture. The methyl ester of tallow fatty acid then remaining after the distillation of the methanol was hydrogenated with the addition of 0.3% by weight of Raney nickel, based on the fatty acid ester charged, in an autoclave at 200°–220° C. under a hydrogen pressure of 20 bar for a period of 2 hours. The hardened methyl ester of tallow fatty acid obtained after separation of the catalyst had the values: iodine number 0.1; hydroxyl number 0; acid number 5.9; saponification number 195.4. This ester was sulfonated in the described manner, neutralized, and bleached. After a bleaching time of 30 minutes, the Klett number of the ester sulfonate paste obtained was 42.

EXAMPLE 15

An unhardened tallow fatty acid, obtained by splitting of tallow and washing out of glycerol, was hydrogenated under the conditions stated in Example 14. The hardened tallow fatty acid was then distilled in the presence of 1% by weight, based on the charged acid, of sodium boron hydride, by heating to a sump temperature of 230° C./0,1 mbar. The distilled tallow fatty acid was then esterified with methanol under the conditions stated in Example 14. The obtained hardened methyl ester of tallow fatty acid with the values: iodine number 0.5; hydroxyl number 0; acid number 5.5; saponification number 198 was sulfonated as described above, and bleached. After a bleaching time of 2 hours, the Klett number of the obtained ester sulfonate paste was 44.

EXAMPLE 16

An unhardened tallow fatty acid, obtained by splitting of tallow and washing out the glycerol, was distilled with addition of 1% by weight, based on the fatty acid charged, of the catalyst from Example 10, by heating to a sump temperature of 230° C./0,1 mbar. The purified tallow fatty acid was esterified with methanol under the conditions stated in Example 14. The methyl ester obtained was hydrogenated under the conditions stated in Example 14. The hardened methyl ester of tallow fatty acid had the values: iodine number 0; hydroxyl number 0; acid number 5.4; saponification number 195.4, and was sulfonated in the stated manner, neutralized, and bleached. After a bleaching time of 30 minutes, the Klett number of the obtained ester sulfonate paste was 50.

EXAMPLE 17

An unhardened tallow fatty acid, obtained by splitting of tallow and washing out the glycerol, was hydrogenated under the conditions stated in Example 14. The hardened tallow fatty acid obtained was distilled with addition of 5% by weight, based on the fatty acid charged, of the catalyst from Example 10, by heating to a sump temperature of 230° C./0,1 mbar. The distilled acid was then esterified with methanol under the conditions stated in Example 14. The hardened methyl ester of tallow fatty acid obtained had the values: iodine number 0.4; hydroxyl number 0; acid number 2.7; saponification number 198, and was sulfonated as described above, neutralized, and bleached. After a bleaching time of 2 hours, the Klett number of the ester sulfonate paste obtained was 38.

The preceding specific embodiments are illustrative of the practice of the invention. It is to be understood, however, that other expedients known to those skilled in the art or disclosed herein may be employed without departing from the spirit of the invention or the scope of the appended claims.

We claim:

1. A process for the preparation of lower alkyl esters of higher fatty acids with improved processing properties comprising the steps of subjecting lower alkyl esters of higher fatty acids of plant and/or animal origin, to a heat treatment above 150° C., in the presence of an effective amount to reduce the hydroxyl number of a material selected from the group consisting of esterification catalysts and carboxylic acid anhydrides, for a time sufficient to effect an improvement in further processing properties, separating purified lower alkyl esters of higher fatty acids from the treated material and recovering said lower alkyl esters of higher fatty acids with improved processing properties.

2. The process of claim 1 wherein said heat treatment was conducted at a temperature of between about 150° to 280° C.

3. The process of claim 1 wherein said heat treatment was conducted at a temperature of between about 200° to 250° C.

4. The process of claim 1 wherein said heat treatment time to effect an improvement in further processing properties is up to about 60 minutes.

5. The process of claim 1 wherein said heat treatment time to effect an improvement in further processing properties is from 0.1 to 60 minutes.

6. The process of claim 1 wherein said heat treatment time to effect an improvement in further processing properties is from 0.1 to 30 minutes.

7. The process of claim 1 wherein said heat treatment time to effect an improvement in further processing properties is from 0.1 to 15 minutes.

8. The process of claim 1 wherein said heat treatment temperature and said heat treatment time to effect an improvement in further processing properties are mutually adjusted so that an esterification or reesterification of free hydroxyl groups present in the starting materials takes place without any other substantial change at the structure of said lower alkyl esters of higher fatty acids.

9. The process of claim 8 wherein said heat treatment temperature is from 200° to 250° C. and said heat treatment time is from 0.1 to 3 minutes.

10. The process of claims 1 wherein said heat treatment is conducted at a subatmospheric pressure.

11. The process of claim 10 wherein said subatmospheric pressure is from 0.1 to 10 torr.

12. The process of claim 1 wherein said subjecting step and said separating step are combined and said separating step is by vacuum distillation.

13. The process of claim 1 wherein said material is an esterification catalyst and is soluble in the starting material and/or in the high-boiling substances formed during said heat treatment.

14. The process of claim 15 wherein said esterification catalyst is essentially neutral to alkaline reacting.

15. The process of claim 1 wherein said material is a high-boiling carboxylic acid anhydride.

16. The process of claim 1 wherein said effective amount to reduce the hydroxyl number is from 0.01 to 10% by weight, based on the higher fatty acid esters or free higher fatty acid starting material.

17. A process for the preparation of lower alkyl esters of higher fatty acids of plant and/or animal origin with improved processing properties consisting essentially of subjecting lower alkyl esters of higher fatty acids of plant and/or animal origin, to a heat treatment at a temperature of from 200° to 250° C. for a heat treatment time of from 0.1 to 3 minutes, in the presence of an effective amount to reduce the hydroxyl number of a material selected from the group consisting of esterification catalysts and carboxylic acid anhydrides, said time sufficient to effect an improvement in further processing properties, vacuum distilling at a subatmospheric pressure of from 0.1 to 10 torr the purified lower alkyl esters of higher fatty acids from the treated material and recovering said lower alkyl esters of higher fatty acids with improved processing properties.

18. The process of claim 17 wherein said starting lower alkyl ester of higher fatty acids of plant and/or animal origin is a hardened methyl ester of a tallow fatty acid.

19. The process of claim 1 wherein said starting lower alkyl ester of higher fatty acids of plant and/or animal origin is a hardened methyl ester of a tallow fatty acid.

* * * * *